(12) United States Patent
Ha et al.

(10) Patent No.: US 8,906,433 B2
(45) Date of Patent: Dec. 9, 2014

(54) **COSMETIC COMPOSITION FOR SKIN MOISTURISATION COMPRISING PINE-RESIN EXTRACT, *PINUS DENSIFLORA* NEEDLE EXTRACT AND *PINUS DENSIFLORA* ROOT EXTRACT**

(71) Applicant: Amorepacific Corporation, Seoul (KR)

(72) Inventors: Jeong Cheol Ha, Yongin-si (KR); Lee Kyoung Kwon, Suwon-si (KR); Youn Joon Kim, Seoul (KR); Ho Sik Rho, Yongin-si (KR); Sang Hoon Han, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 13/892,481

(22) Filed: May 13, 2013

(65) Prior Publication Data

US 2013/0251827 A1    Sep. 26, 2013

Related U.S. Application Data

(62) Division of application No. 13/203,474, filed as application No. PCT/KR2010/001181 on Feb. 25, 2010, now abandoned.

(30) Foreign Application Priority Data

Feb. 27, 2009    (KR) .................. 10-2009-0017079

(51) Int. Cl.
| | |
|---|---|
| *A61K 36/15* | (2006.01) |
| *A61K 36/00* | (2006.01) |
| *A61K 8/97* | (2006.01) |
| *A61Q 19/00* | (2006.01) |

(52) U.S. Cl.
CPC . *A61K 8/97* (2013.01); *A61Q 19/00* (2013.01); *A61Q 19/007* (2013.01)
USPC ............... 424/770; 424/725; 424/773

(58) Field of Classification Search
None
See application file for complete search history.

(56) References Cited

FOREIGN PATENT DOCUMENTS

| FR | 002693371 A1 | 1/1994 |
|---|---|---|
| FR | 2693371 A1 * | 1/1994 |
| JP | 2003-277223 | 10/2003 |
| KR | 2001-017516 A | 3/2001 |
| KR | 2001017516 A * | 3/2001 |
| KR | 10-2007-0074005 | 7/2007 |
| KR | 10-2007-0082635 | 8/2007 |
| KR | 864541 B1 | 10/2008 |
| KR | 864541 B1 * | 10/2008 |

OTHER PUBLICATIONS

Watanabe et al. (Water-Solube polysaccharides from the root of *Pinus densiflora*, Phytochemistry, 1991, vol. 30, No. 5 p. 1425-1429, see abstract).*

Nov. 16, 2012 Singapore Written Opinion and Search Report in Singapore SN 201105621-5 mailed Nov. 16, 2012.

Singapore agent's letter forwarding Search Report and Written Opinion received Dec. 12, 2012.

International Search Report for PCT/KR2010/001181 mailed Nov. 8, 2010.

Watanabe et al (Water-Soluble polysaccharides from the root of *Pinus densiflora*, Phytochemistry, 1991, vol. 30, No. 5 p. 1425-1429).

* cited by examiner

*Primary Examiner* — Chris R Tate
*Assistant Examiner* — Randall Winston
(74) *Attorney, Agent, or Firm* — Nixon & Vanderhye P.C.

(57) ABSTRACT

The present invention relates to a skin moisturizing cosmetic composition that includes a pine resin extract, a *Pinus Densiflora* needle extract, and a *Pinus Densiflora* root extract, as active ingredients. More specifically, the present invention includes a pine resin extract, a Pinus Densiflora needle extract, and a *Pinus Densiflora* root extract, as active ingredients, and has advantageous effects of improving moisturizing activity on the skin and enhancing skin texture, skin clearness and skin contour.

4 Claims, 5 Drawing Sheets

** significance level (p< 0.01)

** significance level (p < 0.01) with respect to 0 week

** significance level (p < 0.01)

\* significance level (p < 0.05) with respect to 0 week
\*\* significance level (p < 0.01) with respect to 0 week

COSMETIC COMPOSITION FOR SKIN MOISTURISATION COMPRISING PINE-RESIN EXTRACT, *PINUS DENSIFLORA* NEEDLE EXTRACT AND *PINUS DENSIFLORA* ROOT EXTRACT

This application is a divisional of Ser. No. 13/203,474 filed Aug. 25, 2011 which in turn is the U.S. national phase of International Application No. PCT/KR2010/001181, filed 25 Feb. 2010, which designated the U.S. and claims priority to KR Application No. 10-2009-0017079, filed 27 Feb. 2009, the entire contents of each of which are hereby incorporated by reference

TECHNICAL FIELD

The present invention relates to a skin moisturizing cosmetic composition containing pine resin extract, *Pinus Densiflora* needle extract and *Pinus Densiflora* root extract as active ingredients, and particularly to, a skin moisturizing cosmetic composition that contains pine resin extract, *Pinus Densiflora* needle extract and Pinus Densiflora root extract as active ingredients and has effects of enhancing moisturizing activity on the skin and improving skin texture, skin clearness and skin contour.

BACKGROUND ART

Pine resin (pine sap) is a material that injured pine trees produce to cover the damaged regions for the sake of self-protection. The pine resin prevents a loss of moisture, and propagation and infiltration of disease-producing microorganisms and has healing effects to prevent necrosis on the injured regions of pine trees.

Among the natural materials for herbal medicine specified in a variety of oriental medicine records and used for folk remedies, the pine resin possesses medical effects on inflammation, gastrointestinal disease, pulmonary tuberculosis, or the like, and a paste of its powder with water is recently reported to be useful as a good facial mask for acne treatment.

On the other hand, among the natural materials for herbal medicine specified in a variety of oriental medicine records and used for folk remedies, the needles of *Pinus Densiflora* indigenous to Korea reportedly have medical effects on liver disease, genitourinary disease, gastrointestinal disease, circulatory disease, cutaneous disease, and so forth, and recently many documents disclose the properties of the *Pinus Densiflora* needle extract, such as aromaticity, antimicrobial property, antioxidant property, and function of inhibiting activation of melanin (Jung et al., Antioxidant principles from the needles of red pine, *Pinus Densiflora*. Phytother Res., 17(9): 1064-1068, 2003). An experiment regarding the pharmacological effects of the *Pinus Densiflora* needles has been reported to reveal the effects of diets introducing pine needles on lipid metabolism in rats, antimicrobial property, antimutagenicity, antioxidant property and antihypertensive property (Kang et al., Korean J. Food Sci. Technol., 27(6): 978-984, 1995).

In the Korean culture, *Pinus Densiflora* Sieb. et Zucc. is a traditional dietary ingredient believed to be a drug for improving life quality for health and longevity, even turning humans into supernatural beings, and a symbol of constancy and fortitude in Korean people, and has different medical effects depending on its parts for a variety of diseases.

Red pine tree, *Pinus Densiflora* is used for medicinal purposes, and the parts of red pine tree come in different names, such as "pine knots" for branch and stem knots; "pine roots" for rudimentary root and root bark; "pine tips" for burgeons or the tips of burgeons; "pine needles" for needle leaves; "pine pollen"; "pine cone"; and "pine bark".

Among these parts, the pine root collected and dried in spring is, according to the oriental medicine records, known to have a bitter taste and a property more warm than cold but no poison. The effective ingredients of the pine root include 75%•-pinene, camphene, dipentene, α-terpineol, camphor, p-methanol, and so forth.

According to the oriental medicine, the pine root is used to remove fatigue and treat bruise, ecchymosis, aching pain, haematemesis, and toothache. However, there is very little academic information on the benefits of pine resin, *Pinus Densiflora* needles and *Pinus Densiflora* root, such as effects of enhancing skin moisturizing activity and improving skin texture, skin clearness and skin contour.

DISCLOSURE

Technical Problem

While researching about pine resin, the inventors of the present invention found out that the pine resin, pine needles and pine root from *Pinus Densiflora* can enhance skin moisturizing activity and improve skin texture, skin clearness, and skin contour, to finally complete the present invention.

Accordingly, it is an object of the present invention to provide a skin cosmetic composition having an excellent skin moisturizing activity.

It is another object of the present invention to provide a skin cosmetic composition having excellent effects of improving skin texture, skin clearness and skin contour.

Technical Solution

To achieve the above objects, the present invention provides a skin moisturizing cosmetic composition containing a pine resin extract, a *Pinus Densiflora* needle extract and a *Pinus Densiflora* root extract, as active ingredients.

Preferably, the cosmetic composition contains the pine resin extract in an amount of 0.001 to 10 wt. % with respect to the total weight of the composition.

Preferably, the cosmetic composition contains the Pinus Densiflora needle extract in an amount of 0.001 to 10 wt. % with respect to the total weight of the composition.

Preferably, the cosmetic composition contains the *Pinus Densiflora* root extract in an amount of 0.001 to 10 wt. % with respect to the total weight of the composition.

Advantageous Effects

The skin cosmetic composition of the present invention contains pine resin extract, *Pinus Densiflora* needle extract and *Pinus Densiflora* root extract as active ingredients, and thus has excellent effects of enhancing skin moisturizing activity and improving skin texture, skin clearness and skin contour.

MODE FOR INVENTION

Figure 1:
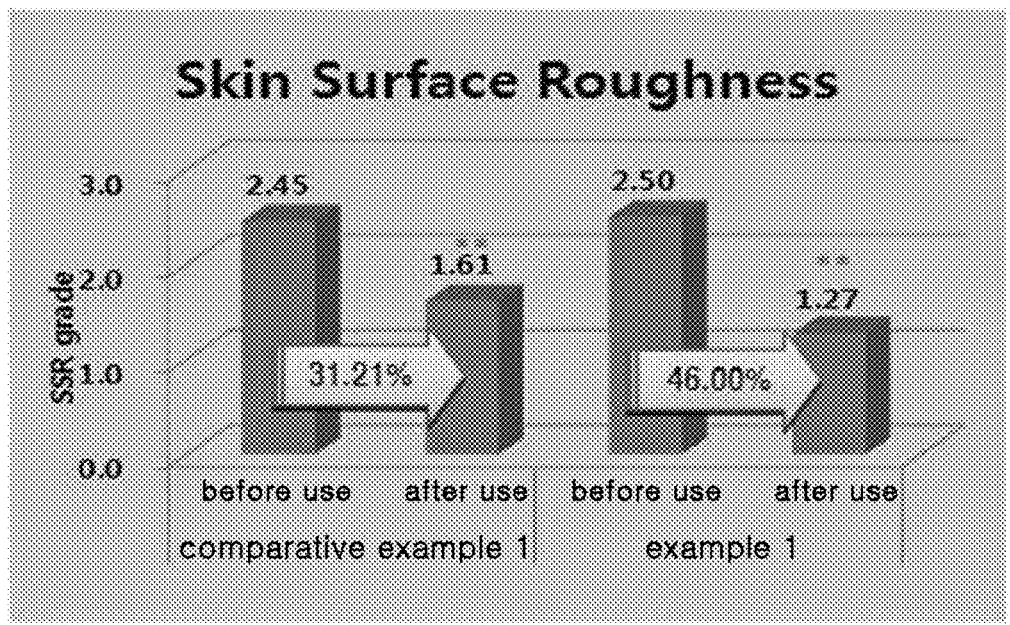
FIG. 1 is a graph showing a change in skin roughness of stratum corneum before and after application of Example 1 and Comparative Example 1.

Hereinafter, the present invention will be described in further detail.

The pine resin as used in the present invention is a material exuded from an injured red pine tree for protecting and healing the injured regions. A botanical list, "Ben Cao Gang Mu (Bon-cho-kang-mok)" says that the pine resin is more warm than cold, tastes bittersweet, and has medical effects on lungs and stomach, reducing stimuli on the skin, providing antimicrobial resistance and healing inflammation. A Korean medical book, "Dongui Bogam" specifies that the pine resin helps to provide comfort to five viscera organs of heart, liver, spleen, lungs and kidneys, remove fever and treat numbness and causes of diseases. The pine resin is also specified to have effects of mitigating malignant boil, tinea capitis, and pruritus, treating alopecia, ear infection and dental cavities from periodontitis, helping skin regeneration, and relieving pains.

To obtain the pine resin extract as used in the present invention, raw pine resin (colophony) is crystallized to collect the product, which is condensed and distilled/captured to remain a portion (40% of the total amount) other than top and bottom portions. After two times of purification, the product undergoes hydrogenation, a third purification and then a distillation to collect a portion (80% of the total amount) other than top and bottom portions.

The skin cosmetic composition of the present invention contains 0.001 to 10 wt. % of the pine resin extract with respect to the total weight of the composition. The content of the pine resin extract less than 0.001 wt. % exerts little effect, and the content of the pine resin exceeding 10 wt. % does not show any prominent increase in the effect pertaining to the raised content.

The *Pinus Densiflora* pine tree as used in the present invention is also called "pine needles", which tastes bitter but is more warm than cold without poison. Traditionally, the pine needles are believed to function on heart and spleen and used for treatment of arthralgia, tinea cruris, syphilitic ulcer, furuncle of leprosy, gout and so forth.

To obtain the *Pinus Densiflora* needle extract as used in the present invention, 50 g of *Pinus Densiflora* needles is exactly weighed, extracted with 70% ethanol at the room temperature for 48 hours, and concentrated by removing the ethanol through vaporization. The concentrated extract can be directly used as a specimen without any further manipulation.

The composition for external application to the skin according to the present invention contains 0.001 to 10 wt. % of the *Pinus Densiflora* needle extract with respect to the total weight of the composition. The content of the Pinus Densiflora needle extract less than 0.001 wt. % exerts little effect, and the content of the *Pinus Densiflora* needle extract exceeding 10 wt. % does not show any prominent increase in the effect pertaining to the raised content.

The process for acquiring the *Pinus Densiflora* root extract as used in the present invention is as follows. First, the *Pinus Densiflora* root is extracted with water or an organic solvent to obtain a germinating plant seed extract. The organic solvent as used herein may include at least one selected from the group consisting of ethanol, methanol, butanol, ether, ethylacetate, or chloroform; or a mixture of the organic solvent and water. Preferably, the organic solvent may be 80% ethanol.

The composition for external application to the skin according to the present invention contains 0.001 to 10 wt. % of the *Pinus Densiflora* root extract with respect to the total weight of the composition. The content of the Pinus Densiflora root extract less than 0.001 wt. % exerts little effect, and the content of the *Pinus Densiflora* root extract exceeding 10 wt. % does not show any prominent increase in the effect pertaining to the raised content.

The composition for external application to the skin according to the present invention contains a cosmetologically and dermatologically acceptable medium and/or base, which is any kind of preparation suitable for topical application, such as, for example, solution, gel, solid or pasty anhydrous product, oil-in-water emulsion, suspension, microemulsion, microcapsules, microgranular or ionic (liposome) and/or nonionic vesicle dispersion form, or cream, skin toner, lotion, powder, ointment, spray or conceal stick form. The composition may be prepared by a preparation method known to those skilled in the art. Furthermore, the composition for external application to the skin according to the present invention may also be used in the form of a foam or aerosol composition further containing a compressed propellant.

The composition for external application to the skin according to the present invention may further include excipients generally used in the cosmetological or dermatological fields, such as, for example, lipid component, organic solvent, solubilizing agent, thickening agent (gelating agent), emollient, antioxidant, suspending agent, stabilizer, foaming agent, fragrance ingredients, surfactants, water, ionic or nonionic emulsifying agent, fillers, chelating agent (metal ion chelating agent), preservatives, vitamins, occlusive, humectants, essence oils, colorants (dye and pigments), hydrophilic or lipophilic active agents, lipid vesicles, or any other ingredients commonly used in cosmetic compositions. These excipients are used in contents generally acceptable in the cosmetology or the dermatology.

Hereinafter, the present invention will be described with reference to Examples and Experimental Examples, which are not intended to limit the scope of the present invention.

Preparation Example 1

Preparation of Pine Resin Extract

To obtain a pine resin extract, 10 kg of raw pine resin (colophony) was crystallized to collect the crystallization product, which was then condensed and distilled/captured to remain a portion (40% of the total amount) other than top and bottom portions. After two times of purification, the product was subjected to hydrogenation, a third purification and then a distillation to collect a portion (80% of the total amount) other than top and bottom portions.

Preparation Example 2

Preparation of *Pinus Densiflora* Needle Extract 50 g of *Pinus Densiflora* needles were exactly weighed, extracted with 70% ethanol at the room temperature for 48 hours, and concentrated by removing the ethanol through vaporization on an evaporator to obtain a *Pinus Densiflora* needle extract.

Preparation Example 3

Preparation of *Pinus Densiflora* Root Extract 1 kg of fresh root parts of *Pinus Densiflora* was put in 5 L of an 80% ethanol aqueous solution for three times of reflux extraction and deposited at 15° C. for one day. After filtration and centrifugation, the filtrate was concentrated under reduced pressure to obtain 173 g of an extract.

Example 1 and Comparative Example 1

Compositions of Example 1 and Comparative Example 1 were prepared in the form of skin toner preparation according to the formulation shown given in Table 1 (Unit: wt. %)

TABLE 1

| Ingredients | Example 1 | Comparative Example 1 |
|---|---|---|
| Preparation Example 1 | 1.0 | 0 |
| Preparation Example 2 | 1.0 | 0 |
| Preparation Example 3 | 1.0 | 0 |
| Purified Water | Balance | Balance |
| Glycerin | 8.0 | 8.0 |
| Butylene Glycol | 4.0 | 4.0 |
| Hyaluronic Acid Extract | 5.0 | 5.0 |
| β-Glucan | 7.0 | 7.0 |
| Carbomer | 0.1 | 0.1 |
| Caprylic/Capric Triglyceride | 8.0 | 8.0 |
| Squalane | 5.0 | 5.0 |
| Cetearyl Glucoside | 1.5 | 1.5 |
| Sorbitan Stearate | 0.4 | 0.4 |
| Cetearyl Alcohol | 1.0 | 1.0 |
| Preservative | q.s. | q.s. |
| Fragrance | q.s. | q.s. |
| Colorant | q.s. | q.s. |
| Triethanolamine | 0.1 | 0.1 |

Experimental Example 1

Immediate Effect on Skin Texture

Figure 2:
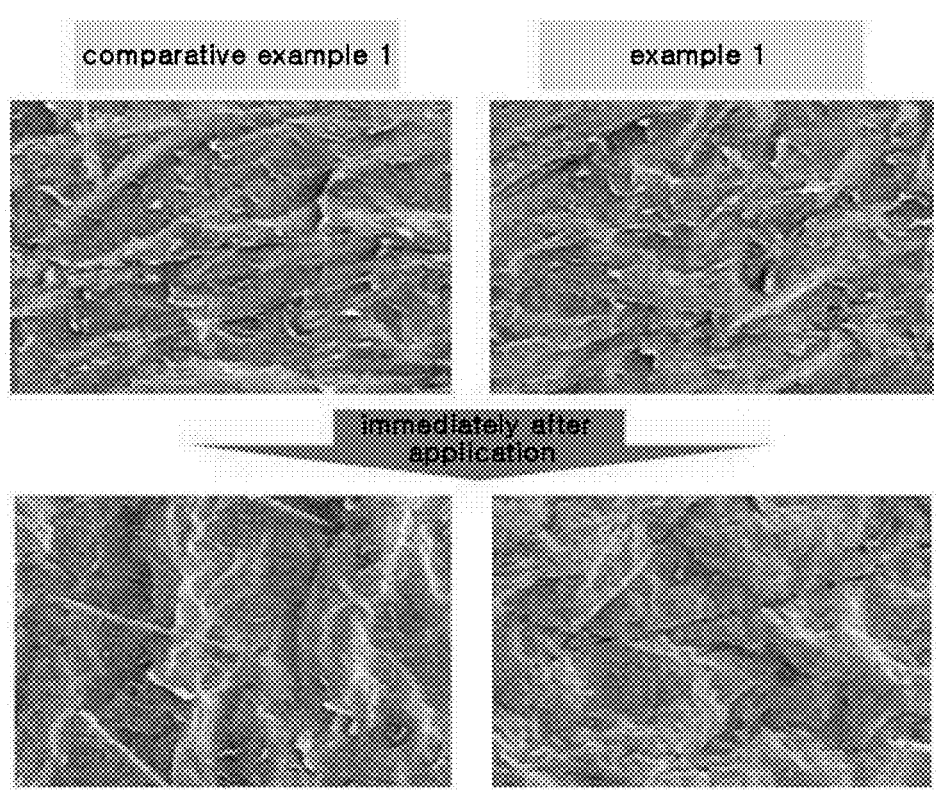
FIG. 2 shows microscopic images of skin texture before and after application of Example 1 and Comparative Example 1.

The preparations of Example 1 and Comparative Example 1 were applied to the skins of the study objects, 40 women in 30 years age group. Immediately after application, the skin texture in stratum corneum was evaluated, and the averaged evaluation results are presented in FIGS. 1 and 2. As a result, the skin surface roughness was improved by 46% with Example 1 and 31% with Comparative Example 1. This shows that the cosmetic composition of the present invention can make the skin texture one and a half time smoother than a general skin toner.

Experimental Example 2

Measurement of Skin Moisture Content

Figure 3:
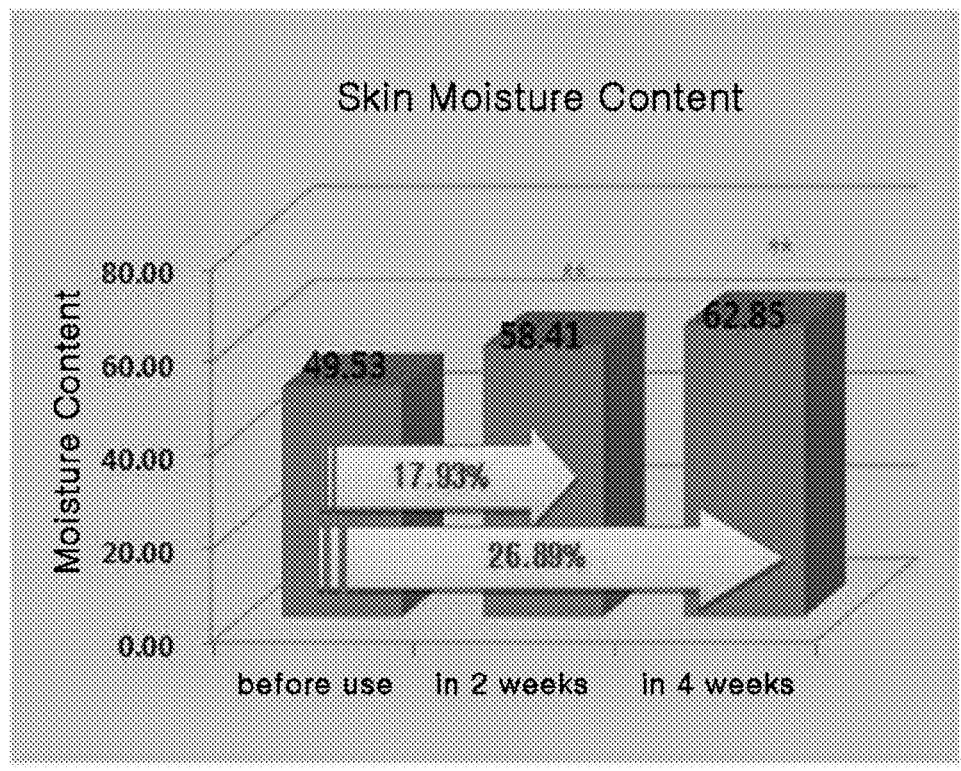
FIG. 3 is a graph showing a change in skin moisture content before and after application of Example 1 and Comparative Example 1.
Figure 4:
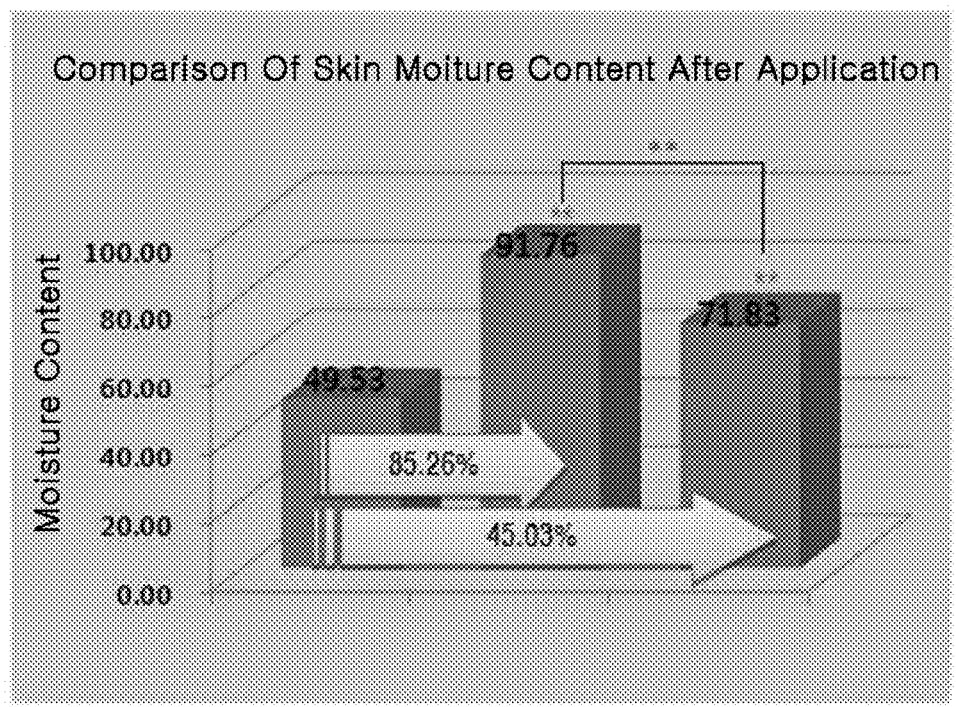
FIG. 4 is graph showing a comparison of skin moisture content immediately after application of Example 1 and Comparative Example 1.

The preparations of Example 1 and Comparative Example 1 were given to the study objects, 40 women in 30 years age group. After 2-week and 4-week uses of each preparation, the skin moisture content was measured. The averaged measurement results are presented in FIGS. 3 and 4. As a result, the preparation of Example 1 improved the skin moisture content by 17.93% in two weeks and 26.89% in four weeks. The cosmetic composition of the present invention was about twice more excellent in the cosmetic effect than a general skin toner.

Experimental Example 3

Improvement of Skin Blood Flow

Figure 5:
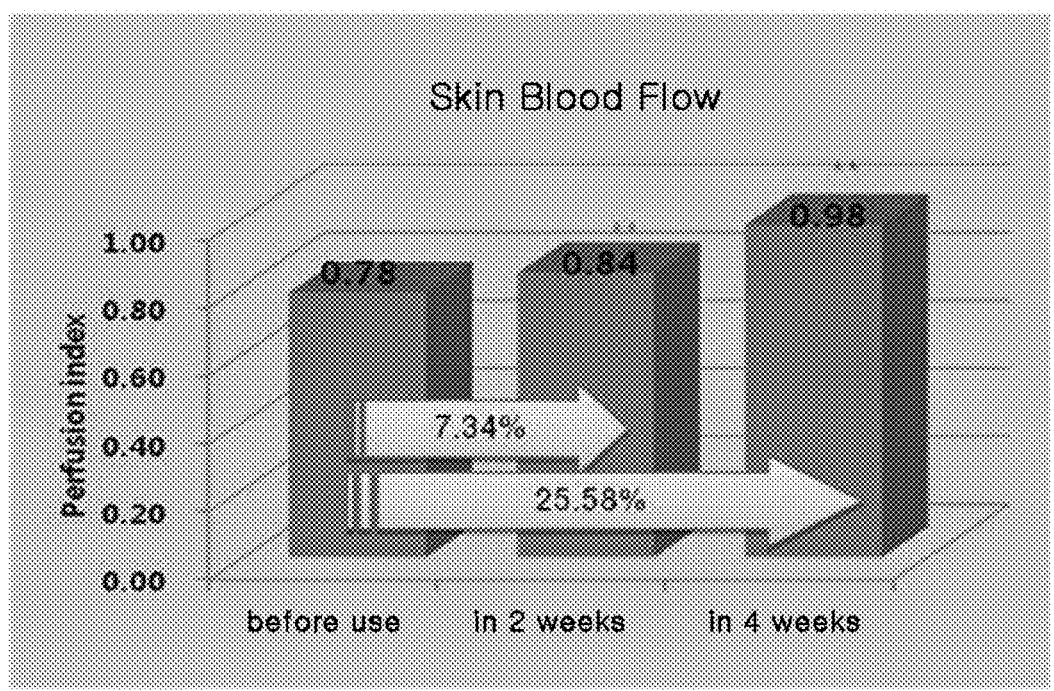
FIG. 5 is a graph showing a change in skin blood flow before and after application of Example 1 and Comparative Example 1.
Figure 6:
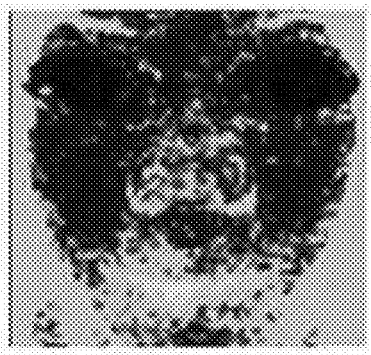
FIG. 6 shows pictures showing a change in skin blood flow before and after application of Example 1 and Comparative Example 1.
Figure 6:
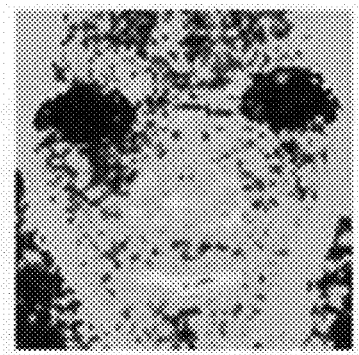
Figure 6:
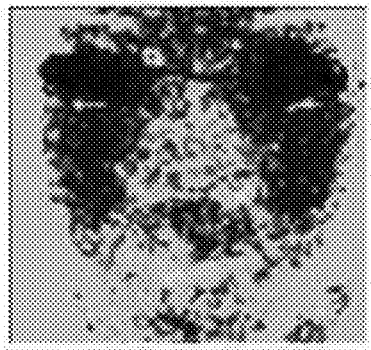
Figure 6:
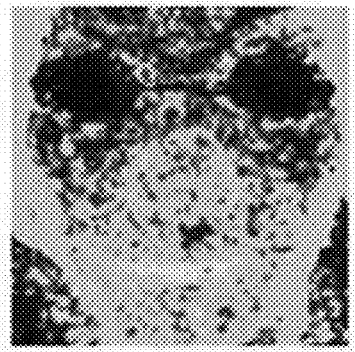
Figure 6:
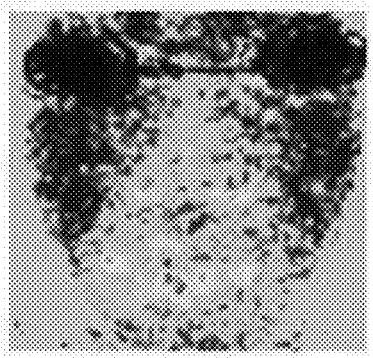
Figure 6:
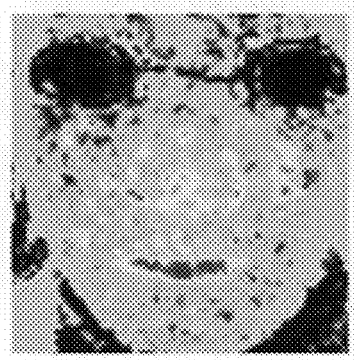

The preparations of Example 1 and Comparative Example 1 were given to the study objects, 40 women in 30 years age group. After 2-week and 4-week uses of each preparation, the skin blood flow was measured. The averaged measurement results are presented in FIGS. 5 and 6. As a result, the preparation of Example 1 improved the skin blood flow by 7.34% in two weeks and 25.58% in four weeks.

Experimental Example 4

Improvement of Skin Lightness and Uniformity

Figure 7:
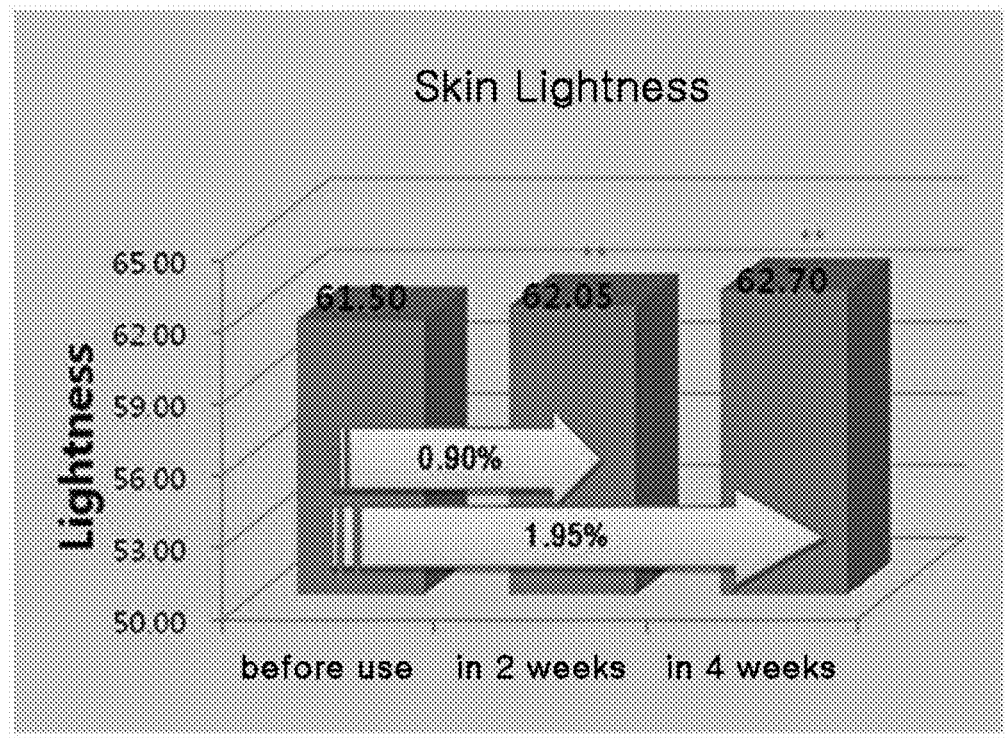
FIG. 7 is a graph showing a change in skin lightness before and after application of Example 1.
Figure 8:
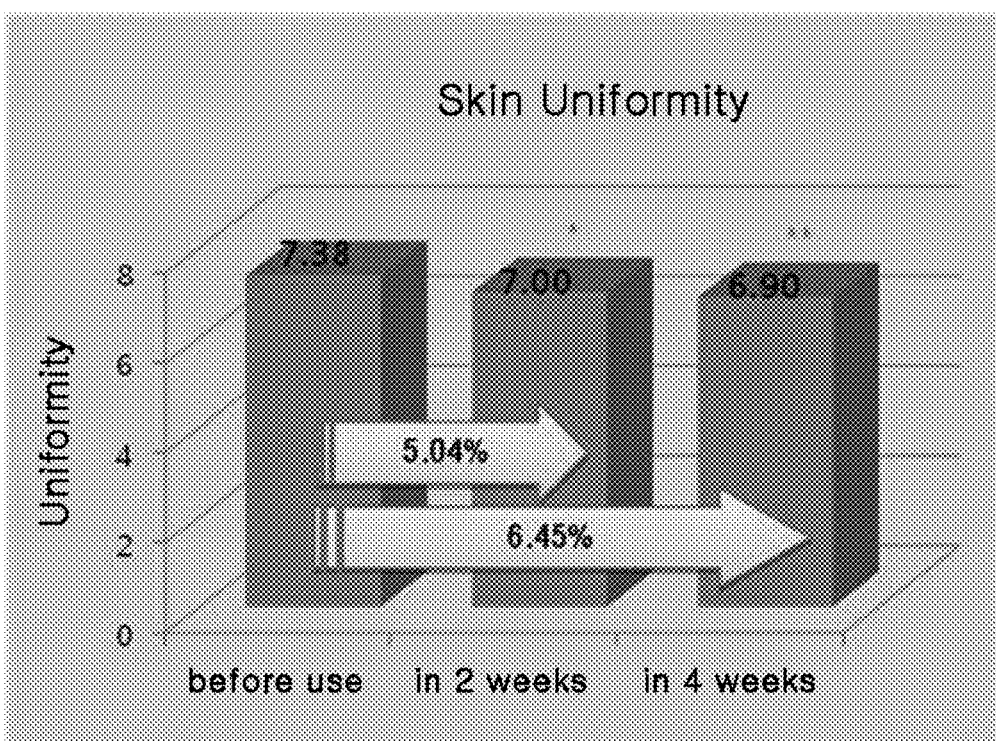
FIG. 8 is a graph showing a change in skin uniformity before and after application of Example 1.

The preparation of Example 1 was given to the study objects, 40 women in 30 years age group. After 2-week and 4-week uses of the preparation, the skin lightness and the skin uniformity were evaluated. The averaged evaluation results are presented in FIGS. 7 and 8. As a result, the preparation of Example 1 increased the skin lightness by 1.95% and improved the skin uniformity by 6.45%.

The invention claimed is:

1. A method of improving skin blood flow comprising topically applying to the skin of a subject in need of same an effective amount of a composition comprising as active ingredients 0.001 to 10 wt % pine resin extract, 0.001 to 10 wt % *Pinus Densiflora* needle extract, and 0.001 to 10 wt % *Pinus Densiflora* root extract, each based on the total weight of the composition.

2. A method of enhancing skin texture comprising topically applying to the skin of a subject in need of same an effective amount of a composition comprising as active ingredients 0.001 to 10 wt % pine resin extract, 0.001 to 10 wt % *Pinus Densiflora* needle extract, and 0.001 to 10 wt % *Pinus Densiflora* root extract, each based on the total weight of the composition.

3. A method of enhancing skin clearness comprising topically applying to the skin of a subject in need of same an effective amount of a composition comprising as active ingredients 0.001 to 10 wt % pine resin extract, 0.001 to 10 wt % *Pinus Densiflora* needle extract, and 0.001 to 10 wt % *Pinus Densiflora* root extract, each based on the total weight of the composition.

4. A method of enhancing skin contour comprising topically applying to the skin of a subject in need of same an effective amount of a composition comprising as active ingredients 0.001 to 10 wt % pine resin extract, 0.001 to 10 wt % *Pinus Densiflora* needle extract, and 0.001 to 10 wt % *Pinus Densiflora* root extract, each based on the total weight of the composition.

* * * * *